United States Patent [19]

Lococo

[11] 4,230,454
[45] Oct. 28, 1980

[54] TOOTH EXTRACTOR

[76] Inventor: Michael P. Lococo, 4927 Victoria Avenue, Niagara Falls, Ontario, Canada, L2E 1X1

[21] Appl. No.: 957,142

[22] Filed: Nov. 3, 1978

[51] Int. Cl.³ .............................................. A61C 3/00
[52] U.S. Cl. .................................. 433/153; 433/157; 433/161
[58] Field of Search .................... 32/61, 62, 43, 44; 254/21, 22; 433/153, 152, 154, 157, 161

[56] References Cited

U.S. PATENT DOCUMENTS

| 178 | 6/1797 | Bruff, Sr. | 32/61 |
|---|---|---|---|
| 1,147,580 | 7/1915 | Turner | 32/62 |
| 1,490,790 | 4/1924 | Wentling | 254/21 |
| 2,428,689 | 10/1947 | Sykes | 433/157 |
| 2,430,271 | 11/1947 | Brantley | 32/61 |
| 3,468,031 | 9/1969 | Mumaw | 32/61 |
| 3,755,901 | 9/1973 | Wilson et al. | 32/43 |

FOREIGN PATENT DOCUMENTS

| 2,718,840 | 11/1978 | Fed. Rep. of Germany | 32/61 |
|---|---|---|---|
| 7,346,673 | 7/1975 | France | 32/61 |

OTHER PUBLICATIONS

"Busch" ad a bur! Journal of Amer. Dental Association, Aug. 1968, Vol. 77, No. 2, pg. 435.

Primary Examiner—Louis G. Mangene
Assistant Examiner—John J. Wilson
Attorney, Agent, or Firm—Stevens, Davis, Miller & Mosher

[57] ABSTRACT

A dentistry kit for tooth extraction consisting of a vise-type grip member having a joint member engaged by a forked end of a lever whose convexly curved fulcrum surface rests against a planar base plate located on teeth adjacent to the extracted tooth. The connection between the grip member and the lever is thus of the type generally resembling an angularly loose swivel joint. The grip member has two hemispherical tips, for engaging correspondingly shaped indentations drilled in the buccal and lingual side of the tooth. The tool set combines a virtually ultimate simplicity of the elements, resulting in an easy cleaning and disinfection, with an improved operation mainly due to the fact that the extreme pull force can be delicately gauged, while the direction of the force can also be changed by displacing the point of contact between the fulcrum and the base plate.

7 Claims, 4 Drawing Figures

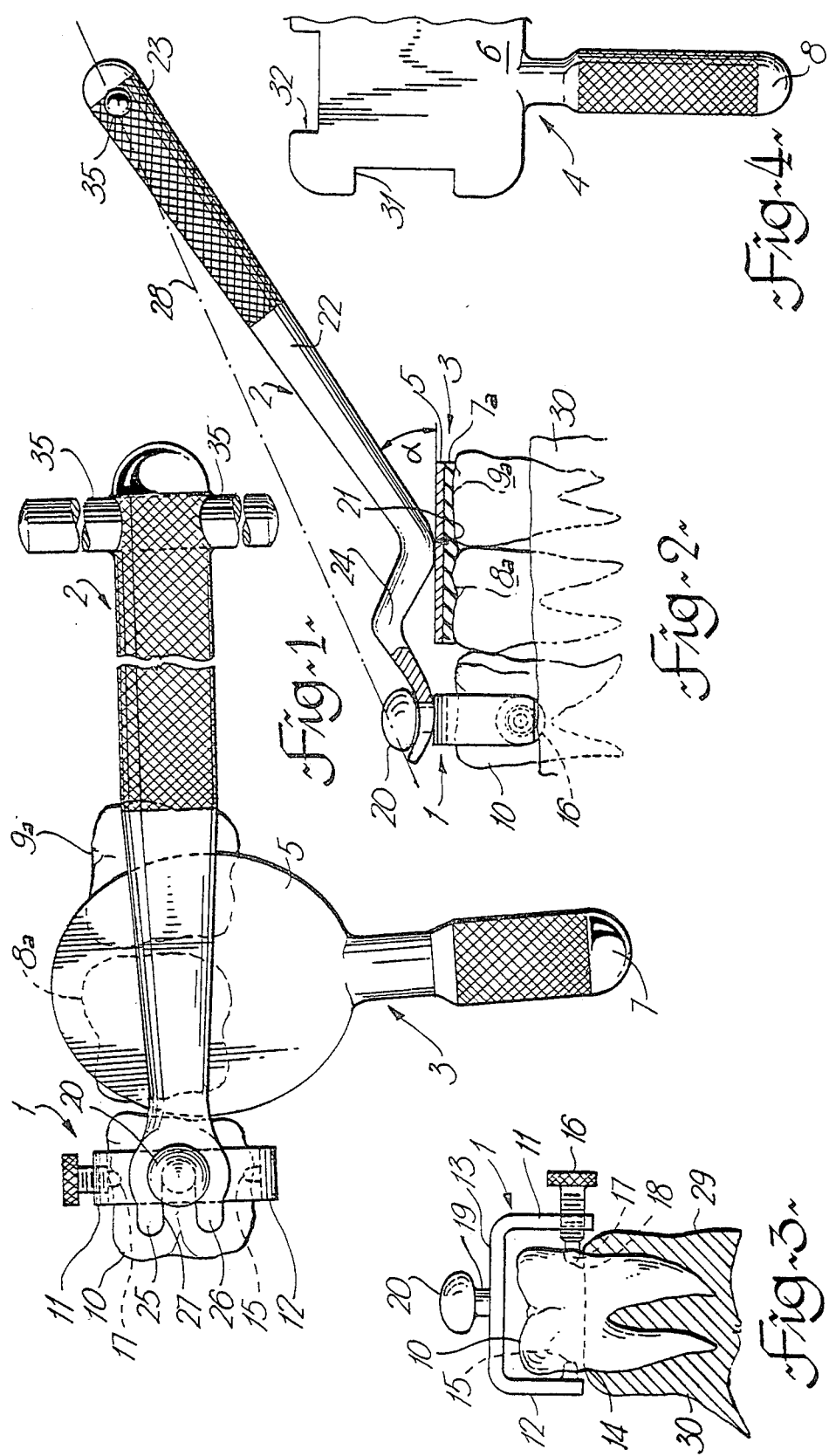

TOOTH EXTRACTOR

The present invention relates to a tooth extracting tool kit of the type comprising a tooth engaging grip means selectively connectable to a lever which, in turn, is rested against a base normally located on a tooth or teeth adjacent the tooth root to be extracted.

In general terms, the tooth extracting tools can be divided into two basic groups, the first group being that of usual pliers such as pliers shown in U.S. Pat. No. 3,456,349 issued July 22, 1969 to W. Heimann. Tooth extracting tools of this kind require considerable force and often their use results in undesirably great damage to the extracted tooth socket.

Therefore, many attempts have been made to overcome the drawback of the pliers-type tools by proposing a tool kit that utilizes three basic elements, namely a base plate rested against the teeth in proximity to the tooth or root to be extracted, a grip element adapted to be firmly secured to the extracted tooth or root and, finally, suitable pull means adapted to engage the grip means such as to pull the tooth out of its socket. The latter group of the extracting sets or kits has the advantage of requiring less physical power from the dentist, thus enabling a more accurate operation which results in a reduced damage of the socket of the extracted tooth with the result of expedient healing after the extraction.

However, the known kits of the above type did not find considerably broad application in practice. Failure of such kits to establish themselves on the market may be attributed to the fact that while minimizing the required physical force during the operation, the tools also reduce the "feel" on the part of the user such that considerable damage to the socket may still occur. Even more important, the relative structural complexity of the known devices gives rise to difficulties in cleaning and disinfecting of such tools.

Many of the tool kits of the above type are arranged to pull the tooth in one direction only, without having the capability of self-adjustment of the direction of pull depending on the shape of the root of the extracted tooth. Still further devices of this type are so complex that they themselves require substantial skill on the part of the dentist to properly operate same.

Reference in the context of the aforesaid comments may be had to the following prior art: U.S. Pat. No. 2,027,470 issued Jan. 14, 1936 to S. T. Caruso; U.S. Pat. No. 2,210,349 issued Aug. 6, 1940 to P. Van Beeck; U.S. Pat. No. 2,430,271 issued Nov. 4, 1947 to W. M. Brantley; and U.S. Pat. No. 2,977,683 issued Apr. 4, 1961 to D. K. Wiltse.

It is an object of the present invention to provide a tooth extracting tool kit of the above type that would not only avoid the complexity of the known devices of the type that would, at the same time improve the convenience of the extraction by making it possible to adjust the general direction of pull effected on the teeth in accordance with the needs, normally dictated by the shape of the root of the respective tooth.

The invention provides, in general terms, a tooth extracting tool kit of the type comprising a a tooth engaging grip means including a joint member for operatively associating the grip means with one end of a two-arm lever means, said lever means having fulcrum means for resting on base means which base means, in turn, is adapted to be rested on the teeth adjacent the tooth to be extracted, wherein said base means is a plate having a generally planar, rigid top surface, said grip means is a generally U-shaped yoke member including two generally coaxial grip elements and adjustment means for selectively adjusting the distance between the grip elements such as to enable the securing of the yoke member to a tooth or root to be extracted, said yoke member further comprises a first joint element, said two-arm-lever means is an uneven-arm lever whose longer arm is provided with a handle and with a crosspiece protruding transversely of the free end of said handle, the shorter arm comprising a second joint element complementary with said first joint element to form with same releasable swivel joint means, the two arm lever further comprising a fulcrum surface adapted to be rested against said rigid top surface, said fulcrum surface being offset relative to a straight line coincident with free ends of the respective arms of said lever means, whereby said lever generally resembles the shape of a check mark.

Preferably, the grip means includes a generally U-shaped, rigid yoke member including two sides and a base interconnecting same, said grip elements being disposed near free ends of the respective side and having generally hemispherical, inwardly turned tips adapted to engage indentations prepared in the buccal and lingual side, respectively, of the tooth or root to be extracted.

It is also preferred that said first joint element be a stem with a convexly shaped head protruding from the base of the yoke member in a direction opposite to that of said sides; said second joint element being a forked end of said lever, including two generally parallel prongs, the spacing between the two being slightly in excess of the diameter of said stem but considerably less than that of the convexly shaped head. The adjustment means is preferably a setscrew threadably received in one of said sides, the free end of said setscrew forming one of said tips, whereby the selective adjustment of the distance between the grip elements can be effected by turning said setscrew. The size and shape of the tips is preferably generally identical with that of a standard burr for use in high speed air turbine driven dentistry drill.

In another aspect of the present invention as defined in general terms, grip means is provided for use in a tooth extracting tool kit of the type comprising a tooth engaging grip means including a joint member for operatively associating the grip means with one end of a two-arm lever means, said lever means having fulcrum means for resting the lever on base means, said base means, in turn, being adapted to be rested on the teeth adjacent to the tooth to be extracted, said grip means being generally U-shaped, rigid yoke member including two generally coaxial grip elements and adjustment means for selectively adjusting the distance between the grip elements such as to enable the securing of the yoke member to a tooth or root to be extracted, said yoke member further comprising a first joint element for releasably securing said yoke member to a lever.

In a still further aspect of the present invention, the invention provides, for use in a tooth extracting tool kit of the type comprising a tooth engaging grip means including a joint member for operatively associating the grip means with the end of a two-arm lever means, said lever means having fulcrum for resting on base means, said base means, in turn, being adapted to be rested on the teeth adjacent to the tooth to be extracted; a set comprising said grip means and said two-arm lever means, wherein said grip means is a generally U-shaped yoke member including two generally coaxial grip elements and adjustment means for selectively adjusting the distance between the grip elements such as to enable the securing of the yoke member to a tooth or root to be extracted; said yoke member further comprises a first joint element; said two-arm-lever means is an uneven-arm lever whose longer arm is provided with a handle and with a cross-piece protruding transversely of the free end of said handle, the shorter arm comprising a second joint element complementary with said first joint element to form with said releasable swivel joint means, the two-arm-lever further comprising a fulcrum surface adapted to be rested against a base means, said fulcrum surface being offset relative to a straight line coincident with free ends of the respective arms of said lever, whereby said lever generally resembles the shape of a check mark.

In a still further aspect of the present invention, lever means is provided for use in a tooth extracting tool kit of the type comprising a tooth engaging grip means including a joint member for operatively associating the grip means with one end of a two-arm lever means, said lever means having fulcrum means generally coincident with base means adapted to be rested on the teeth adjacent to the tooth to be extracted, wherein said two-arm lever means is an uneven-arm lever whose longer arm is provided with a handle and with a cross-piece protruding transversely of the free end of said handle, the shorter arm comprising a second joint element complementary with said joint member to form with same releasable swivel joint means, the two-arm lever further comprising a fulcrum surface adapted to be rested against said base means, said fulcrum surface being offset relative to a straight line coincident with the ends of the respective arms of said lever, whereby said lever generally resembles the shape of a check mark.

The invention will now be described by way of a preferred embodiment with reference to the accompanying, simplified drawings in which FIG. 1 is a plan view of a tooth extracting tool kit according to the preferred embodiment of the present invention, schematically indicated in operation;

FIG. 2 is a side view, partly in section, of FIG. 1;

FIG. 3 is a partial front view of the arrangement shown in FIG. 1 but showing only grip means of the kit according to the present invention; and FIG. 4 shows a plan view of a base member alternative to that shown in FIG. 1.

The extraction tool kit of the present invention is comprised of three basic elements which combine with each other during the use of the invention. Reference 1 denotes what is generally referred to as grip means, the part referred to with 2 can also be referred to as "two-arm lever means" while reference 3 relates to base means, 4 designating a modification of the latter (FIG. 4).

Turning firstly to the base means 3 as shown in FIGS. 1 and 2, the base means is a small, planar plate 5, 6, which is made of stainless steel and is integral with a relatively short handle 7, 8. The plate 5 is thus relatively rigid to support the lever means 2 during the operation, as best shown in FIG. 2. The plate 3, 4, is provided on its underside with a soft, relatively flexible rubber padding 7a (only shown in FIG. 2) which is fixedly secured to plate 5 or 6, for instance by vulcanizing.

In operation, the plate 5 or 6 is rested on teeth such as teeth 8a, 9a adjacent to a tooth 10 which is to be extracted.

Turning now to the grip means 1 and referring to FIG. 3, the grip means 1 is a generally U-shaped yoke having two generally parallel sides 11, 12 and a base 13 interconnecting the sides 11, 12 as shown. Thus, the sides 11, 12 and the base 13 form a rigid, integral unit. Near the free end of side 12 is provided a grip element of the type of an inwardly turned tip 14 whose size and shape is generally identical with a regular burr for use in an air turbine driven dentistry drill (the burr and the drill not shown). Accordingly, the tip 14 can relatively exactly engage an indentation 15 in the tooth 10 to be extracted.

Near the free end of side 11 is threadably received a setscrew 16 whose free end terminates in a hemispherical tip 17 whose configuration is identical to that of the aforesaid tip 14.

The tip 17 is also received in an indentation 18, which is prepared in the same way as the aforesaid indentation 14. Thus, the tips 14, 17 are inwardly turned tips engaging indentations prepared in the buccal (tip 17) and lingual (tip 14) side, respectively of the tooth 10 to be extracted.

Disposed centrally of base 13 is a joint member comprised of a stem 19 terminating at a spherical head 20. The stem 19 and head 20 thus present one embodiment of what generally can be referred to as "a first joint element". As best seen in FIG. 3, the stem protrudes from the base 13 in a direction opposite to that of the sides 11, 12. With reference to FIG. 2, the lever means 2 forms a two-arm lever, having a fulcrum surface 21 (also referred to as "fulcrum means") which is convexly curved and is arranged to normally rest on plate 5. The fulcrum surface 21 divides the lever means 2 into a longer arm 22 provided with grip or handle 23 and with a cross-piece 35 protruding transversely to both sides of the free end of said handle 23, and a shorter arm 24 whose free end is forked and includes two prongs 25, 26 (FIG. 1), defining therebetween a slot 27 whose width is slightly in excess of the diameter of stem 19, but substantially smaller than the diameter of the head 20. As best seen in FIG. 2, the forked end of the lever is preferably concavely curved, to improve the engagement between lever 2 and the grip means 1. The operativeness of the lever is further improved by the particular disposition of the fulcrum surface 21 indicated in FIG. 1. It will be seen from this figure that the location of surface 21 is offset relative to a straight axis 28 coincident with the respective free ends of the arms of lever means 2. In operation, the indentations 15, 18 are first drilled in the tooth 10 to be extracted, in a generally coaxial arrangement. The grip means 1 is then secured to the tooth 10 as shown in FIG. 3, by turning the setscrew 16 until the whole grip means 1 is more or less fixedly secured to the tooth 10. The plate 5 is then placed with rubber padding 7 down, on adjacent teeth 8, 9, whereupon the lever 2 can be applied as shown in FIGS. 1 or 2. By periodically applying and releasing the pressure at the handle 23, not only is the tooth 10 gradually released from its socket but, more important, the fulcrum surface 21 is allowed to find a new point of contact with plate 5 after each release, thus contributing to the main pull force component acting at tooth 10 to be generally coincident with the extension of the root section of the tooth. In some instances, particularly in complicated extractions, it is desirable that the extracted tooth or root be also subjected to luxation, i.e. a side-ward motion in order to release the tooth and/or the root from the socket. The cross-piece 35 enables such motion by making it possible to impart to the handle 23 and thus to the entire lever 2 a twisting or transversely tilting motion relative to the axis 28.

If it is desired to use the device according to the present invention in pulling a root, an incision is made in the buccal side 29 of the gum and in the lingual side 30 of same. Indentations similar to 14, 18 are then provided in the teeth and the operation effected as above. In the latter operation, however, one would use a different size of the grip means 1 which would have longer arms or sides 12, 13.

The advantage of the present invention is in the extreme simplicity that makes it very easy to properly disinfect the set whenever necessary. Furthermore, the possibility of shifting the point of contact between fulcrum surface 21 and plate 5 is of an extreme advantage since it allows the dentist to select appropriate direction of pulling force applied to the tooth 10. Since the head 20 and the forked end 25, 26 of the lever 2 actually form a releasable swivel joint, the dentist can even shift the position of the contact between the fulcrum surface 21 and the plate 5 sidewise (i.e. up or down as viewed in FIG. 1), so that the convenience of operation is further enhanced.

The extreme force of pulling the tooth can be applied delicately and can be gauged with precision.

Those skilled in the art will readily appreciate many further modifications of the preferred embodiment. For instance one can visualize a plate member shown in FIG. 4 which is provided with recesses 31, 32 and 33, the recesses being of the size making it possible to surround at least a part of the sides 12, 11 of the grip means 1. The arrangement generally resembling a swivel joint, of head 20 and fork prongs 25, 26 can be replaced by an arrangement wherein the head 20 would be flat, even though it is believed that the concavo-convex arrangement shown in the preferred embodiment is preferable. Obviously, a plurality of different sizes of the grip means 1, of different shapes of the plate members 5 or 6, would still fall within the scope of the present invention. Similarly one can visualize an arrangement wherein the elements of the "swivel joint" as referred to above would be reversed relative to the grip means 1 and lever means 2.

A still further readily conceivable modification may combine the base means 3 with an auxiliary base, preferably of a relatively thick soft material, for use as a support for the base means 3 on tissue if there are no teeth adjacent to the tooth to be extracted.

These and many other modifications of the preferred embodiment, however, still fall within the scope of the present invention as defined in the accompanying claims.

The embodiments of the invention in which an exclusive property or privilege is claimed are defined as follows:

1. A tooth extracting tool kit of the type comprising a tooth engaging grip means including a joint member for operatively associating the grip means with one end of a two arm lever means, said lever means having fulcrum means adapted to be rested on base means, said base means, in turn, being adapted to be rested on the teeth or tissue adjacent to the tooth to be extracted, wherein:

(a) said base means is a plate having a generally planar, rigid top surface;
(b) said grip means is a generally U-shaped, rigid yoke member including two sides and a base interconnecting same, two generally coaxial grip elements and adjustment means for selectively adjusting the distance between the grip elements such as to enable the securing of the yoke member to a tooth or root to be extracted said grip elements being disposed one near each free end of the respective side and having generally hemispherical, inwardly turned tips adapted to engage indentations prepared in the buccal and lingual side of the tooth or root to be extracted, respectively;
(c) said yoke member further comprises a first joint element;
(d) said two arm lever means is an uneven-arm lever whose longer arm is provided with a handle and with a cross piece protruding transversely of the free end of said handle, the shorter arm comprising a second joint element complementary with said first joint element to form with same releasable swivel joint means, the two-arm lever further comprising a fulcrum surface adapted to be rested against said rigid top surface, said fulcrum surface being offset relative to a straight line coincident with free ends of the respective arms of said lever means, whereby said lever generally resembles the shape of a check mark;
(e) said first joint element being a stem with a convexly shaped head protruding from the base of the yoke member in a direction generally opposite to that of said sides; said second joint element being a forked end of said lever, including two generally parallel prongs, the spacing between the two being slightly in excess of the diameter of said stem but considerably less than that of the convexly shaped head.

2. A kit as claimed in claim 1, wherein said adjustment means is a setscrew threadably received in one of said sides, the free end of said setscrew forming one of said tips, whereby the selective adjustment of the distance between the grip elements can be effected by turning said setscrew.

3. A kit as claimed in claim 1 wherein the size and shape of said tips is generally identical with that of a standard burr for use in high speed air turbine driven dentistry drill.

4. A tool kit as claimed in claim 1, comprising a plurality of said grip means differing from each other in the length of and/or spacing between said two sides.

5. For use in a tooth extracting tool kit of the type comprising a tooth engaging grip means including a joint member for operatively associating the grip means with the end of a two-arm lever means, said lever means having fulcrum means adapted to rest on base means, said base means, in turn, being adapted to be rested on the teeth or tissue adjacent to the tooth to be extracted; a set comprising said grip means and said two-arm lever means, wherein (a) said grip means includes a generally U-shaped, rigid yoke member including two sides and a base interconnecting same, two generally coaxial grip elements being disposed one near each free end of the respective side and having generally hemispherical, inwardly turned tips adapted to engage indentations prepared in the buccal and lingual side, respectively, of the tooth or root to be extracted, and adjustment means for selectively adjusting the distance between the tips of the grip elements such as to enable the securing of the yoke member to a tooth or root to be extracted;

(b) said yoke member further comprises first joint element;

(c) said two-arm lever means is an uneven-arm lever whose longer arm is provided with a handle and with a cross piece protruding transversely of the free end of the said handle, the shorter arm comprising a second joint element complementary with said first joint element to form with same releasable swivel joint means, the two-arm lever further comprising a fulcrum surface adapted to be rested against a base means, said fulcrum surface being offset relative to a straight line coincident with free ends of the respective arms of said lever, whereby said lever generally resembles the shape of a check mark;

(d) said first joint element being a stem with a convexly shaped head protruding from the base of the yoke member in a direction opposite to that of said sides; said second joint element being a forked end of said lever, including two generally parallel prongs, the spacing between the two prongs being slightly in excess of the diameter of said stem but considerably less than that of the convexly shaped head.

6. A set as claimed in claim 5, wherein said adjustment means is a setscrew threadably received in one of said sides, the free end of said setscrew forming one of said tips, whereby the selective adjustment of the distance between the grip elements can be effected by turning said setscrewe.

7. A set as claimed in claims 5 or 6, comprising a plurality of said grip means differing from each other in the length of and/or spacing between said two sides.

* * * * *